United States Patent
Carlson et al.

(10) Patent No.: US 8,196,239 B2
(45) Date of Patent: *Jun. 12, 2012

(54) CLINICAL SUPPORT PAD

(75) Inventors: Delroy W. Carlson, North St. Paul, MN (US); Christopher J. Zwettler, Stillwater, MN (US)

(73) Assignee: Micropulse, Inc., North St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/285,555

(22) Filed: Oct. 31, 2011

(65) Prior Publication Data

US 2012/0042453 A1 Feb. 23, 2012

Related U.S. Application Data

(63) Continuation of application No. 12/512,842, filed on Jul. 30, 2009, now Pat. No. 8,051,516.

(60) Provisional application No. 61/084,647, filed on Jul. 30, 2008.

(51) Int. Cl.
*A47C 27/10* (2006.01)

(52) U.S. Cl. .................................. 5/710; 5/712; 5/655.3

(58) Field of Classification Search ............... 5/710–714, 5/655.3
See application file for complete search history.

(56) References Cited

U.S. PATENT DOCUMENTS

| | | | |
|---|---|---|---|
| 4,005,236 A | 1/1977 | Graebe | |
| 4,707,872 A | 11/1987 | Hessel | |
| 4,896,389 A | 1/1990 | Chamberland | |
| 5,010,608 A | 4/1991 | Barnett et al. | |
| 5,533,220 A | 7/1996 | Sebag et al. | |
| 5,561,875 A | 10/1996 | Graebe | |
| 5,564,142 A | 10/1996 | Liu | |
| 5,652,987 A | 8/1997 | Fujita | |
| 5,901,393 A | 5/1999 | Pepe et al. | |
| 5,906,019 A | 5/1999 | McCarthy et al. | |
| 5,907,878 A | 6/1999 | Thomas et al. | |
| 5,926,884 A | 7/1999 | Biggie et al. | |
| 6,302,988 B1 | 10/2001 | Miller, Sr. | |
| 6,442,780 B1 | 9/2002 | Phillips et al. | |
| 6,550,085 B2 | 4/2003 | Roux | |
| 6,584,628 B1 | 7/2003 | Kummer et al. | |

(Continued)

FOREIGN PATENT DOCUMENTS

EP 1874250 A2 1/2008

(Continued)

*Primary Examiner* — Michael Trettel
(74) *Attorney, Agent, or Firm* — Brooks, Cameron & Huebsch, PLLC

(57) ABSTRACT

The present disclosure includes methods, devices, and systems associated with clinical support. In one embodiment, a clinical support pad includes a plurality of support cells formed in a first film layer of material sufficiently impermeable to a fluid contained in the cells such that each cell is configured to be alternately and repeatedly inflated and deflated with respect to one or more adjacent cells. Each cell is in fluid communication with at least one of a number of channels formed in the first film layer, is configured such that a surface of each cell has a continuous curvature across a length direction and across a width direction of the cell, and are spaced such that a distance between a center of each cell and a center of at least one adjacent cell is not more than a two-point discrimination threshold distance associated with a patient.

19 Claims, 7 Drawing Sheets

U.S. PATENT DOCUMENTS

| | | |
|---|---|---|
| 6,874,185 B1 | 4/2005 | Phillips et al. |
| 7,168,116 B2 | 1/2007 | Reger et al. |
| 7,278,179 B2 | 10/2007 | Schneider |
| 8,051,516 B2 * | 11/2011 | Carlson et al. .................. 5/710 |
| 2004/0226102 A1 | 11/2004 | Hampton et al. |

FOREIGN PATENT DOCUMENTS

WO 2006087545 A2 8/2006

* cited by examiner

CLINICAL SUPPORT PAD

CROSS-REFERENCE TO RELATED APPLICATION

This application is a Continuation of U.S. application Ser. No. 12/512,842, filed Jul. 30, 2009, now U.S. Pat. No. 8,051,516, which is a Non-Provisional Application of U.S. Provisional Application Ser. No. 61/084,647, filed Jul. 30, 2008, the entire contents of which are incorporated herein by reference.

BACKGROUND

Persons may become confined to a support surface such as a bed, wheel chair, or other device, for a large variety of reasons (e.g., as a result of injury or illness or as a consequence of the requirements of a job function during employment). Also, elderly persons may be confined to beds or other devices for extended periods of time.

Decubitus ulcers, which are also referred to as pressure ulcers, pressure sores, and/or bedsores, are a pervasive problem in the health care field, with high cost both in terms of individual human suffering and in the financial cost to society. Decubitus ulcers are localized cellular necroses that tend to develop when soft tissue is compressed between a bony prominence and a firm surface for prolonged periods of time. External pressure exerts its influence by occluding blood flow, leading to ischemic injury. Interruption of blood flow, and hence oxygen supply, can cause a sequence of intracellular events to occur, which proceeds to an irreversible stage if the blood flow is not restored. Ischemic injury can result in cell death and the accumulation of cell debris within the tissues.

Factors affecting the formation of decubitus ulcers include the intensity and duration of the pressure being applied. If a patient remains immobile and in the same position for periods of time that are less than about two hours, the ischemia may be reversible and generally no long term or irreversible damage is done to the soft tissues (e.g., skin, subcutaneous tissues, and muscle) over bony prominences. However, if the period of immobility exceeds a certain threshold (e.g., about two hours), decubitus ulcers begin to form.

To prevent the formation of decubitus ulcers, it is the policy of many hospitals and institutions to reposition patients about every two hours. However, this practice can be physically intensive and less than effective. In addition, there is a trend towards the care of patients in the home, rather than in a hospital, and in such circumstances nursing care may not be available for twenty four hours/day.

There are a variety of systems available that are intended to reduce the formation of decubitus ulcers. Various previous approaches include static devices (e.g., foam mattresses, air mattresses, water beds and sheepskins), which attempt to redistribute support away from bony prominences, and active devices (e.g., alternating air mattresses), which function by alternately shifting support pressure.

One example of an active device is discussed in U.S. Pat. No. 5,010,608 to Barnett et al., which describes a support system having a plurality of separate cells that are alternately and repeatedly inflated. The distance between centers of adjacent cells is less than the human two-point discrimination threshold. However, such previous approaches have various drawbacks. For instance, the configuration (e.g., spacing, shape, etc.) of the separate cells in previous approaches can lead to drawbacks such as susceptibility to leaking, patient discomfort, and/or manufacturing inefficiency, among other drawbacks.

DETAILED DESCRIPTION

Figure 1A:
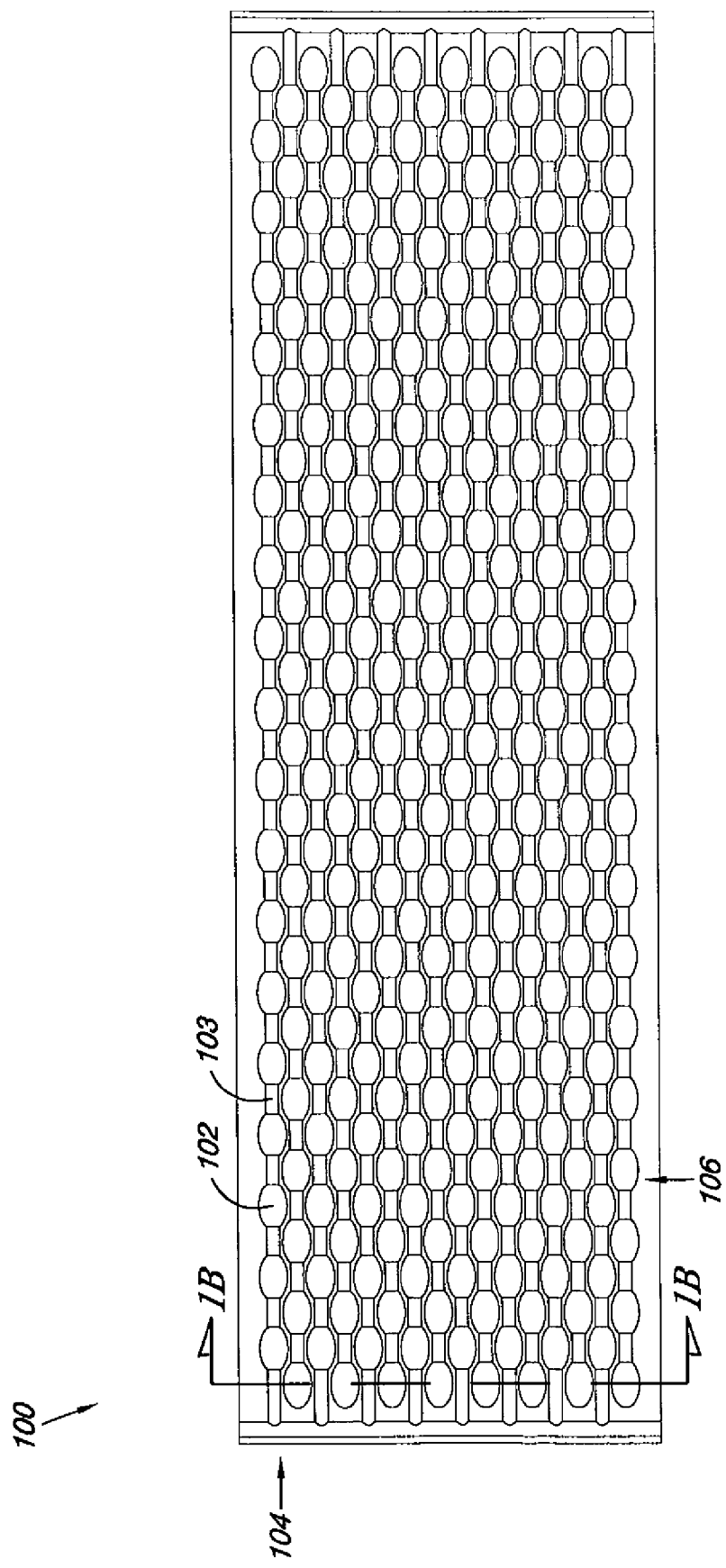
FIG. 1A is an overhead view of a clinical support pad in accordance with one or more embodiments of the present disclosure.

The present disclosure includes methods, devices, and systems associated with clinical support. Various embodiments can provide benefits such as reducing or eliminating the occurrence of decubitus ulcers (e.g., bedsores or pressure sores). In one embodiment, a clinical support pad includes a plurality of support cells formed in a first film layer of material sufficiently impermeable to a fluid contained in the cells such that each cell is configured to be alternately and repeatedly inflated and deflated with respect to one or more adjacent cells. Each cell is in fluid communication with at least one of a number of channels formed in the first film layer, is configured such that a surface of each cell has a continuous curvature across a length direction and across a width direction of the cell, and are spaced such that a distance between a center of each cell and a center of at least one adjacent cell is not more than a two-point discrimination threshold distance associated with a patient.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

As used herein, "a number of" something can refer to one or more such things. For example, a number of memory devices can refer to one or more memory devices.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure, and should not be taken in a limiting sense.

FIG. 1A is an overhead view of a clinical support pad 100 in accordance with one or more embodiments of the present disclosure. In various embodiments, and as illustrated in FIG. 1, the pad 100 includes a plurality of support cells 102 formed in a first layer of material (e.g., layer 108 shown in FIG. 1D) that is sufficiently impermeable to a fluid contained in the cells such that each cell 102 is configured to be alternately and repeatedly inflated and deflated with respect to one or more adjacent cells. A number of channels 103 are also formed in the first layer, and each cell 102 is in fluid communication with at least one of the number of channels 103.

The material in which the cells 102 and channels 103 are formed can be various materials including, but not limited to, a polymeric material such as polyethylene, polypropylene, polyvinyl chloride, polyvinylidene chloride, polyester, polyamide, chlorosulphonated polyethylene, vinylidene fluoride/hexafluoropropylene copolymers, polyurethane, ethylene/propylene/diene terpolymers, copolyetherester polymers, silicon rubber, butyl rubber and natural rubber, coated if necessary, to obtain appropriate permeability properties. One of ordinary skill in the art will appreciate that the material in which the cells 102 and channels 103 are formed can depend on factors such as the type of fluid (e.g., air or other gas, water, gel, etc.) contained in the cells 102.

In various embodiments, and as illustrated in FIG. 1A, the cells 102 of pad 100 are arranged in a number of columns 104 and rows 106. In the embodiment illustrated in FIG. 1A, the cells 102 of adjacent columns 104 are staggered such that the cells 102 of next adjacent columns 104 are aligned as rows 106 of cells 102. However, embodiments of the present disclosure are not limited to the example illustrated in FIG. 1A.

In the embodiment illustrated in FIGS. 1A-1E, each of the plurality of support cells 102 is configured such that a surface 107 of each cell 102 has a continuous curvature across a length direction and across a width direction of the cell 102. As used herein, a surface having a "continuous curvature" intends that an equation describing the surface is continuous in the second derivative (e.g., the radius of curvature of the surface has no discontinuities).

As an example, an ellipsoidal shape has a continuous curvature across its surface and can be described by the equation:

$$\frac{x^2}{a^2} + \frac{y^2}{b^2} + \frac{z^2}{c^2} = 1$$

for an axis-aligned body in an xyz Cartesian coordinate system where a and b are the equatorial radii (along the x and y axes) and c is the polar radius (along the z-axis). If a, b, and c are equal, then the above equation would describe a sphere. The values of a, b, and c can be adjusted to describe various other shapes such as oblate spheroids, prolate spheroids, or triaxial ellipsoids, for instance.

Providing cells 102 having a continuous curvature across one or more of a length and a width direction can provide various benefits over previous support systems. For instance, surfaces which do not have a continuous curvature can be more prone to leaking due to one or more discontinuities in the curvature. For example, the separate cells described in U.S. Pat. No. 5,010,608 have a number of essentially vertical flat side faces and a rounded top surface, such that a discontinuity exists at the transitions between the side walls and top surface. This discontinuity can cause the cells to be prone to leaking through repeated use (e.g., repeated inflation/deflation) over time. Although the cells 102 illustrated in FIGS. 1A-1E are ellipsoidal in shape, embodiments are not limited to a particular shape.

In various embodiments, and as illustrated in FIG. 1A, the plurality of support cells 102 are spaced such that a distance between a center of each cell and a center of at least one adjacent cell is not more than a two-point discrimination threshold distance associated with a patient. In various embodiments, the pad 100 is configured such that the centers of adjacent inflated cells are not more than the two-point discrimination threshold distance associated with the patient. As used herein, "two point discrimination threshold distance" is measured on a person's back, being the minimum distance at which two objects may be distinguished by touch when the objects are placed on the skin, that distance being understood in the anatomy profession and being approximately 25 mm (millimeters) on a person's back.

In embodiments in which the cells 102 are spaced such that the centers of adjacent inflated cells are less than the two point discrimination threshold distance, a patient lying or sitting on the pad 100 is unable to distinguish by touch that alternate cells are inflated and deflated. Also, the patient is generally unable to sense the deflation of cells (e.g., cells 105-2 shown in FIG. 1C) and inflation of cells (e.g., cells 105-1 shown in FIG. 1C) of support pad 100.

As such, clinical support pads and support systems of the present disclosure can provide alternating support for a patient in a manner such that the patient has little or no sensation of the alternating support being provided by the support pad (e.g., support pad 100). That is, parts of the patient's body are alternately being supported and not supported with the patient having little or no sensation of movement in the bed on which they are lying (or chair on which they are sitting), for instance. Such sensation could cause discomfort to and/or be disconcerting to the patient.

In some embodiments, the pad 100 is configured such that the centers of adjacent inflated cells in the anterior/posterior direction of a patient are not more than 20 mm apart. In various embodiments, the cells 102 of pad 100 are configured such that a width direction of the cells corresponds to the anterior/posterior direction of the patient and a length direction of the cells corresponds to a direction transverse to the anterior/posterior direction of the patient.

Additionally, in various embodiments, the pressure exerted on the patient's body juxtaposed to a deflated cell is less than the human internal capillary threshold (e.g., 20-32 mm Hg). Capillary pressure threshold refers to the surface pressure above which capillaries can be expected to collapse and is about 20-32 mm Hg, depending on factors such as the patient and the area of the patient in contact with the support pad 100. Configuring the support pad 100 such that pressure exerted on the body by deflated cells is less than the human internal capillary threshold can prevent loss of blood circulation to the particular area of the patients skin over the deflated cells, which can prevent formation of decubitus ulcers.

Figure 1B:
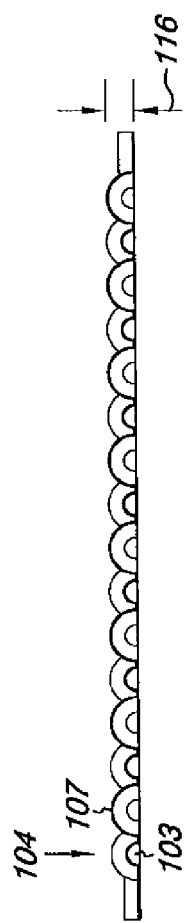
FIG. 1B is a cross-sectional view of the clinical support pad shown in FIG. 1A.

FIG. 1B is a cross-sectional view of the clinical support pad 100 shown in FIG. 1A. In the embodiment illustrated in FIG. 1B, the cells 102 are configured such that the distance between the centers of cells in next adjacent columns 104 is 20 mm (e.g., see distance 114 shown in FIG. 1E), which is less than the two-point discrimination threshold distance associated with a patient. As such, the distance between adjacent inflated cells along a width direction of the cells is 20 mm. Also, as shown in the embodiment illustrated in FIG. 1B, the surface 107 of the cells has a continuous curvature in the width direction of the cells.

The embodiment shown in FIG. 1B also illustrates the height 116 of the support cells. In various embodiments, the height 116 of the cells does not exceed 6.5 mm when in the inflated state. In some embodiments, the height 116 of the cells is not greater than 6 mm when in the inflated state. Configuring cells 102 such that they have a relatively small height as compared to previous approaches can provide various benefits.

For instance, a relatively small height (e.g., below about 6.5 mm) of inflated cells can reduce the movement of a patient due to the alternating inflation/deflation of the support cells 102, while still maintaining effectiveness by not bottoming out under the weight of the patient and exerting a pressure less than the human internal capillary threshold on the body of the patient when the cells are in the deflated condition. As used herein, bottoming out can refer to collapse of a support cell of a clinical support pad such that the top portion of the cell comes into contact with the underlying or bottom portion of the cell under the influence of the weight of a patient, as well as to contact by the patient with the underlying portion of the clinical support pad between the support cells.

Reduced patient movement due to alternating inflation/deflation of the cells can allow clinical support pads of the present disclosure to be used in operating rooms, where movement of the patient may hinder an operating procedure, for example. Cells having a reduced height as compared to previous approaches can also provide benefits such as a reduction in shear stress associated with movement of a patient on the support pad, and can improve ease of manufacture of the support pad, among other benefits.

Figure 1C:
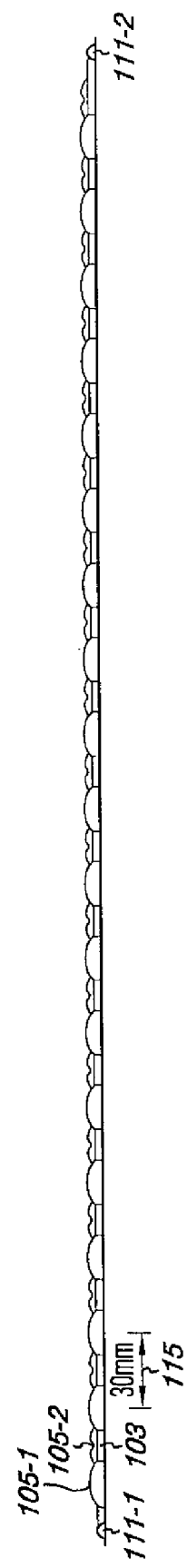
FIG. 1C illustrates a number of cells in an inflated condition and a number of cells in a deflated condition in accordance with one or more embodiments of the present disclosure.

FIG. 1C illustrates a number of cells 105-1 in an inflated condition and a number of cells 105-2 in a deflated condition in accordance with one or more embodiments of the present disclosure. In the embodiment illustrated in FIG. 1C, the cells are spaced such that the distance 115 between centers of adjacent inflated cells 105-1 is 30 mm along a length direction of the cells. Also, the cells are spaced such that the distance between centers of adjacent deflated cells 105-2 is also 30 mm along a length direction of the cells.

In the embodiment illustrated in FIG. 1C, the inflated cells 105-1 form a column of cells (e.g., column 104) that are in fluid communication with each other via channels 103 therebetween. Similarly, the deflated cells 105-2 form an adjacent column of cells that are in fluid communication with each other via channels (not visible in FIG. 1C). The cells 105-1 are coupled to a conduit 111-1 and the cells 105-2 are coupled to a conduit 111-2, which can each be coupled to an inflation/deflation source (e.g., inflation/deflation source 462 shown in FIG. 4) and used to inflate and/or deflate the respective cells in an alternating manner.

As described below in connection with FIG. 1E, the conduit 111-1 and the conduit 111-2 can each be coupled to columns of cells in an alternating manner. For example, the conduit 111-1 may be coupled to the odd numbered columns (e.g., first, third, fifth, etc.), while the conduit 111-2 may be coupled to the even numbered columns (e.g., second, fourth, six, etc.). As such, alternating columns of cells can be inflated and deflated together as a group via conduits 111-1 and 111-2.

Figure 1D:
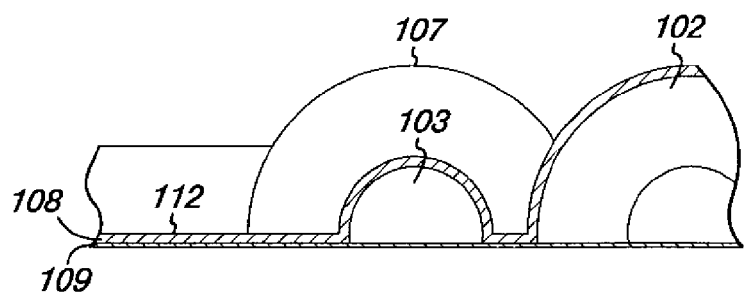
FIG. 1D is a cross-sectional view of a portion of the clinical support pad shown in FIG. 1A.

FIG. 1D is a cross-sectional view of a portion of the clinical support pad 100 shown in FIG. 1A. FIG. 1D illustrates a first film layer 108 of impermeable material in which a number of support cells 102 and channels 103 are formed. In various embodiments, and as illustrated in FIG. 1D, the support pad 100 includes a planter backing layer 109 attached to the first layer 108.

The backing layer 109 can be attached to the first film layer 108 in various manners including, but not limited to, lamination or heat bonding. Attachment of the backing layer 109 to the first layer 108 creates a seal between the base surface 112 of the first layer 108 and the backing layer 109, which forms the cavities of the support cells 102 and channels 103 of the support pad 100.

As illustrated in FIG. 1D, the surface 107 of the cells 102 has a continuous curvature across the width direction of the cell. That is, the continuous curvature begins and ends on the base surface 112 of the first film layer 108.

Figure 1E:
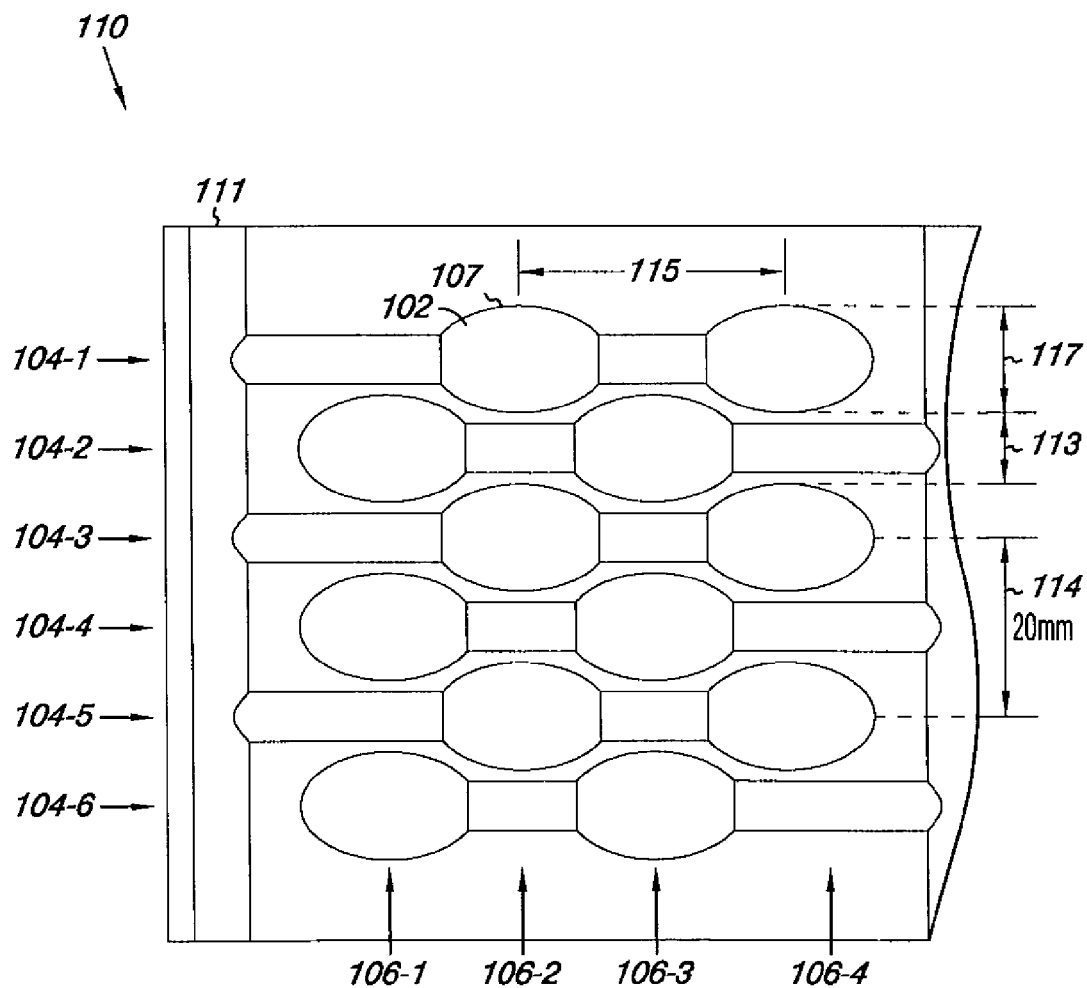
FIG. 1E is an overhead view of a portion of the clinical support pad shown in FIG. 1A.

FIG. 1E is an overhead view of a portion 110 of the clinical support pad 100 shown in FIG. 1A. As illustrated in FIG. 1E, the portion 110 includes a plurality of support cells 102 configured to be alternately and repeatedly inflated and deflated with respect to one or more adjacent cells.

In the embodiment illustrated in FIG. 1E, the portion 110 includes a number of columns of cells 104-1, 104-2, 104-3, 104-4, 104-5, and 104-6, with the cells 102 of adjacent columns being staggered such that cells of next adjacent columns are aligned as rows 106-1, 106-2, 106-3, and 106-4. The cells 102 of the first column 104-1, third column 104-3, and fifth column 104-5 are in fluid communication with each other via channels 103. The cells 102 of the second column 104-2, fourth column 104-4, and sixth column 104-6, are in fluid communication with each other.

In various embodiments, and as shown in FIG. 1E, cells 102 of alternating adjacent (e.g., every other) columns are in fluid communication with each other such that the cells are inflated and deflated substantially concurrently. For instance, the columns 104-1, 104-3, and 104-5 are each coupled to conduit 111, which can receive a fluid (e.g., air or other suitable fluid) from an inflation/deflation source (not shown in FIG. 1E). Similarly, the columns 104-2, 104-4, and 104-6 are each coupled to conduit (not shown in FIG. 1E) coupled to an inflation/deflation source for substantially concurrent inflation/deflation in an alternating manner with the cells of the columns 104-1, 104-3, and 104-5.

In various embodiments, and as illustrated in FIG. 1E, a distance 113 between an edge of a particular support cell 102 of a first column (e.g., 104-1) and an edge of a particular support cell 102 of a third column (e.g., 104-3) is less than a greatest width 117 of the particular support cell 102 of the first column 104-1 and of the particular support cell 102 of the third column 104-3, in relation to an axis perpendicular to the first column and third column. As such, the edges of cells 102 in adjacent columns (e.g., 104-1 and 104-2) overlap in both a length and a width direction. Configuring the cells 102 in this manner can improve the spacing of the cells 102 as compared to previous support pad approaches.

The improved spacing can allow the dimensions of the cell (e.g., length, width, height) to be more suitably configured for patient comfort by maintaining a two-point discrimination threshold distance (e.g., 114) between the centers of adjacent inflated and/or deflated cells, while preventing bottoming out under the weight of the patient and while exerting a pressure of less than the human internal capillary threshold on the body of the patient with the deflated cells. Also, the relatively small size of the cells 102 can decrease the time required to inflate supporting cells and deflate adjacent cells as compared to previous approaches, which can provide an appropriate pressure relief phase (e.g., an interface pressure below internal capillary pressure) of sufficient duration to allow normal blood flow and tissue recovery, among other benefits.

Figure 2A:
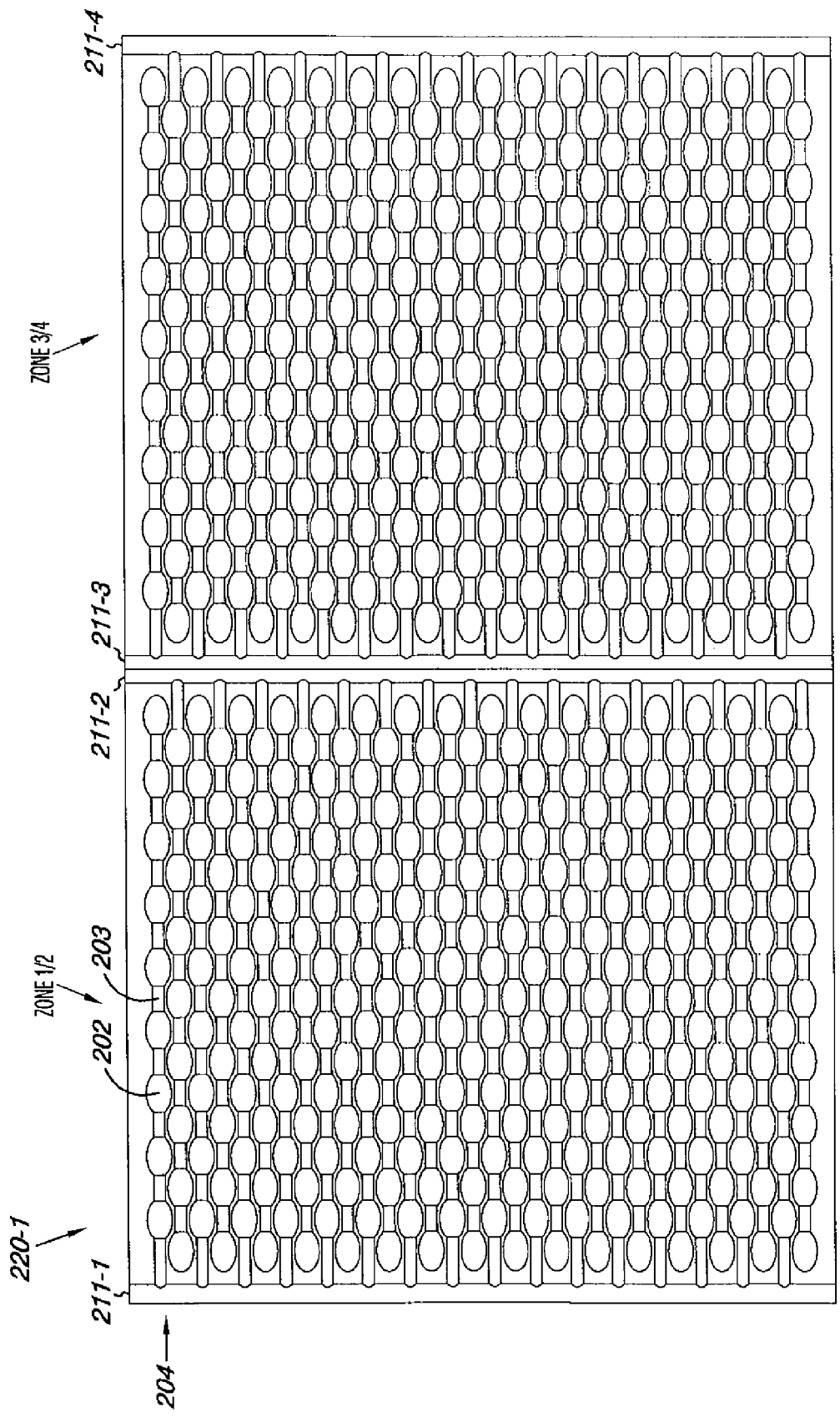
FIG. 2A is an overhead view of a clinical support pad in accordance with one or more embodiments of the present disclosure.

FIG. 2A is an overhead view of a clinical support pad 220-1 in accordance with one or more embodiments of the present disclosure. The support pad 220-1 includes a plurality of support cells 202 each in fluid communication with at least one channel 203. As described above in connection with FIGS. 1A-1E, the cells 202 are arranged in rows 206 and columns 204, with the cells of adjacent columns 204 being staggered such that cells of next adjacent columns are aligned as rows 206 of cells. Also, as described above, the cells 202 are configured such that a surface of each cell has a continuous curvature in at least one of a length direction and a width direction of the cells. In this example, the upper surface of cells has an ellipsoidal shape having a continuous curvature in both the length and width direction of the cells 202.

In various embodiments, and as illustrated in FIG. 2A, each of the plurality of support cells 202 is associated with one or more of a number of zones of cells (e.g., zone 1, zone 2, zone 3, and zone 4), with the cells of each zone configured for inflation and deflation substantially concurrently. In one or more embodiments, the number of zones is at least four. In some embodiments, the cells of each of at least two of the number of zones are in an inflated condition while the cells of at least two of the number of zones are in a deflated condition.

In the example illustrated in FIG. 2A, each zone of cells is in fluid communication with a corresponding conduit 211-1, 211-2, 211-3, and 211-4. That is, the cells of zone 1, zone 2, zone 3, and zone 4 are in fluid communication with conduits 211-1, 211-2, 211-3, and 211-4, respectively. Each of the conduits 211-1, 211-2, 211-3, and 211-4 are coupled to a control component (not shown in FIG. 2A) that can include an inflation/deflation source to provide repeated inflation and deflation of the cells in each of the zones in an alternating manner.

Figure 2B:
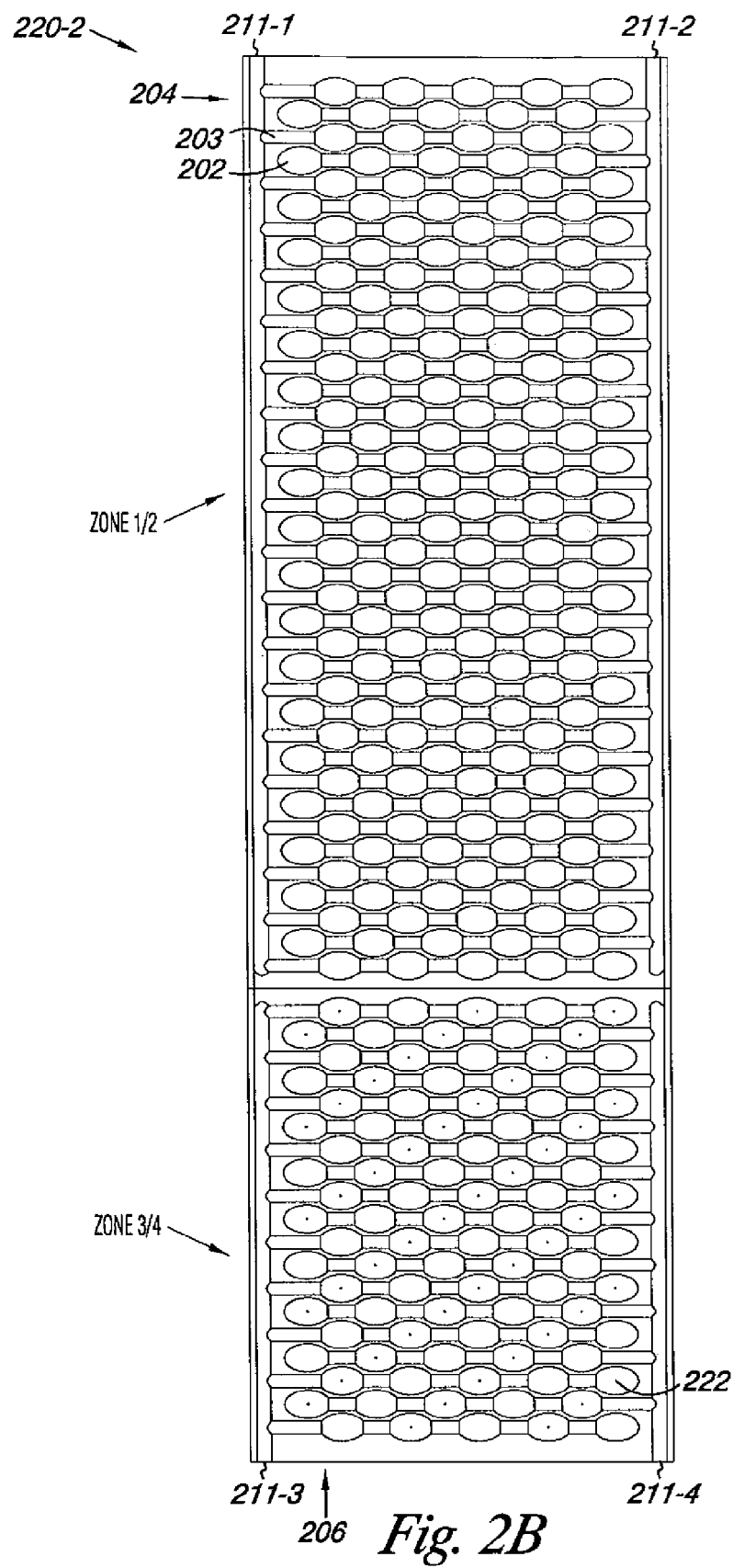
FIG. 2B is an overhead view of a clinical support pad in accordance with one or more embodiments of the present disclosure.

FIG. 2B is an overhead view of a clinical support pad 220-2 in accordance with one or more embodiments of the present disclosure. The support pad 220-1 includes a plurality of support cells 202 each in fluid communication with at least one channel 203. As described above in connection with FIGS. 1A-1E, the cells 202 are arranged in rows 206 and columns 204, with the cells of adjacent columns 204 being staggered such that cells of next adjacent columns are aligned as rows 206 of cells. Also, as described above, the cells 202 are configured such that a surface of each cell has a continuous curvature in at least one of a length direction and a width direction of the cells. In this example, the upper surface of cells has an ellipsoidal shape having a continuous curvature in both the length and width direction of the cells 202.

In the embodiment illustrated in FIG. 2B, each of the plurality of support cells 202 is associated with one or more of a number of zones of cells (e.g., zone 1, zone 2, zone 3, and zone 4), with the cells of each zone configured for inflation and deflation substantially concurrently. In the example illustrated in FIG. 2B, each zone of cells is in fluid communication with a corresponding conduit 211-1, 211-2, 211-3, and 211-4. That is, the cells of zone 1, zone 2, zone 3, and zone 4 are in fluid communication with conduits 211-1, 211-2, 211-3, and 211-4, respectively. Each of the conduits 211-1, 211-2, 211-3, and 211-4 are coupled to a control component (not shown in FIG. 2A) that can include an inflation/deflation source to provide repeated inflation and deflation of the cells in each of the zones in an alternating manner.

In various embodiments, and as illustrated in FIG. 2B, selected ones of the plurality of support cells 202 include an orifice 222 providing fluid communication between an interior and an exterior of the cells 202 such that fluid contained therein is gradually released causing the cells to change from an inflated condition to a deflated condition. Providing selected cells having an orifice 222 can be used to achieve a peristaltic effect as the cells 202 without the orifice 222 deflate at a different rate than cells not having the orifice 222. A peristaltic effect can thus be achieved without the need for additional tubing (e.g., additional conduits).

In the embodiment illustrated in FIG. 2B, only selected cells within zone 3 (e.g., cells 202 coupled to conduit 211-3) and within zone 4 (e.g., cells 202 coupled to conduit 211-4) include an orifice 222. As such, only the cells of zones 3 and 4 are configured for a peristaltic effect. Providing a peristaltic effect in particular areas, while not providing it in others may be beneficial for creating a preferred direction of net blood flow in a particular area of a patient's body. For instance, the effect can be used to direct blood from a patient's lower extremities, to reduce swelling in that area, for example. Embodiments of the present disclosure not limited to the examples described in connection with FIG. 2B.

Figure 3A:
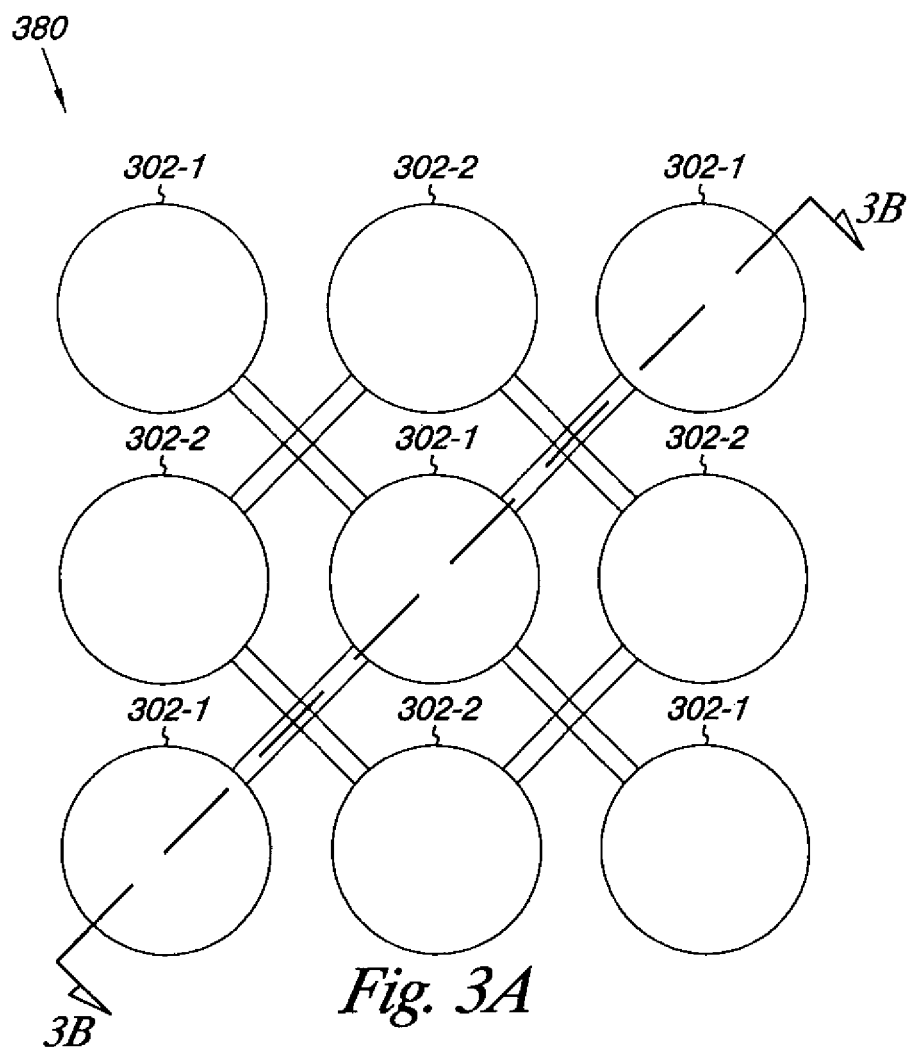
FIG. 3A is an overhead view of a clinical support pad in accordance with one or more embodiments of the present disclosure.
Figure 3B:
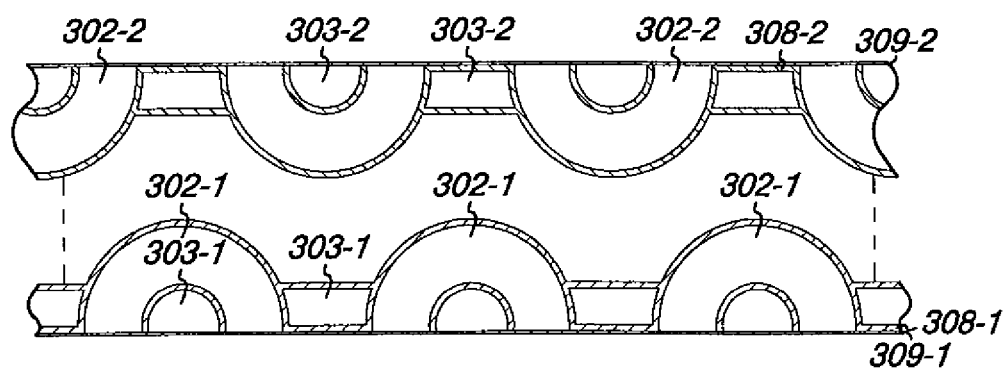
FIG. 3B is an exploded cross-sectional view of the clinical support pad shown in FIG. 3A.
Figure 3C:
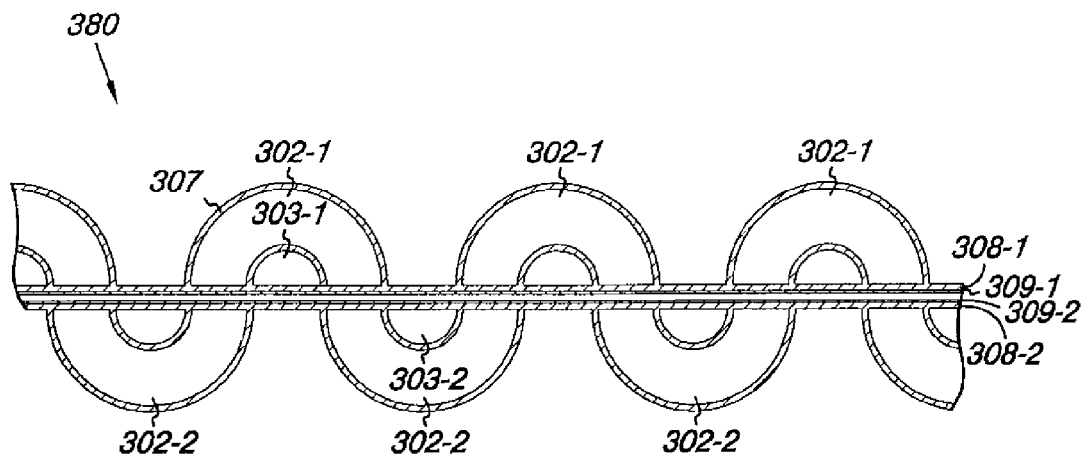
FIG. 3C is a side view of the clinical support pad shown in FIG. 3A.

FIG. 3A is an overhead view of a clinical support pad 380 in accordance with one or more embodiments of the present disclosure. FIG. 3B is an exploded cross-sectional view of the clinical support pad 380 shown in FIG. 3 according to one or more embodiments. FIG. 3C is a side view of the clinical support pad 380 shown in FIG. 3A, according to a different embodiment.

The support pad 380 illustrated in FIGS. 3A, 3B, and 3C includes a plurality of support cells 302-1 formed in a layer of material 308-1 and a plurality of support cells 302-2 formed in a layer of material 308-2.

In the embodiment illustrated in FIGS. 3A, 3B, and 3C, the support cells 302-1 are in fluid communication with each other via channels 303-1 formed in the layer 308-1, and the support cells 302-2 are in fluid communication with each other via channels 303-2 formed in the layer 308-2. A backing layer 309-1 is attached to the layer 308-1 and a backing layer 309-2 is attached to the layer 308-2. The layers 308-1, 308-2, 309-1, and 309-2 can be flexible layers of a polymeric material, for example. The backing layers 309-1 and 309-2 can be attached to the respective layer 308-1 and 309-1 in various manners including, but not limited to, lamination or heat bonding.

In the embodiment illustrated in FIGS. 3A, 3B, and 3C, the pad 380 is configured such that each of the cells 302-1 are inflated and deflated concurrently and in alternating manner with the cells 302-2, which are also inflated and deflated concurrently. Configuration of the cells 302-1 and 302-2 as illustrated in FIGS. 3A, 3B, and 3C can allow for a relatively small distance (e.g., about 10 mm) between centers of adjacent cells 302-1 and 302-2.

In the embodiment illustrated in FIGS. 3A, 3B, and 3C, the cells 302-2 formed in layer 308-2 are the same as the cells 302-1 formed in layer 308-2, but the cells 302-2 and 302-1 are offset by half of the pitch associated with the cells. As such, the cells 302-2 are positioned between respective cells 302-1. Forming a pad 380 in accordance with the embodiment illustrated in FIGS. 3A, 3B, and 3C can decrease the spacing between opposing cells 302-1 and 302-2 without a need to leave room for fusion of the layers.

In the embodiment illustrated in FIGS. 3A, 3B, and 3C, the cells 302-1 and 302-2 have a spheroid shape. As such, the surface 307 of the cells 302-1 and 302-2 is continuous in both a length and a width direction of the cells.

In the embodiment illustrated in FIG. 3B, the cells 302-1 formed in layer 308-1 are located between the cells 302-2 formed in layer 308-2 when the pad is in operation. That is, the cells 302-1 and 302-2 are sandwiched between each other when the layers are stacked together.

In contrast, in the embodiment illustrated in FIG. 3C, the layer of cells 302-1 and the layer of cells 302-2 are positioned back to back. In one or more embodiments, the backing layers 309-1 and 309-2 may or may not be attached (e.g., adhered to each other).

Figure 4:
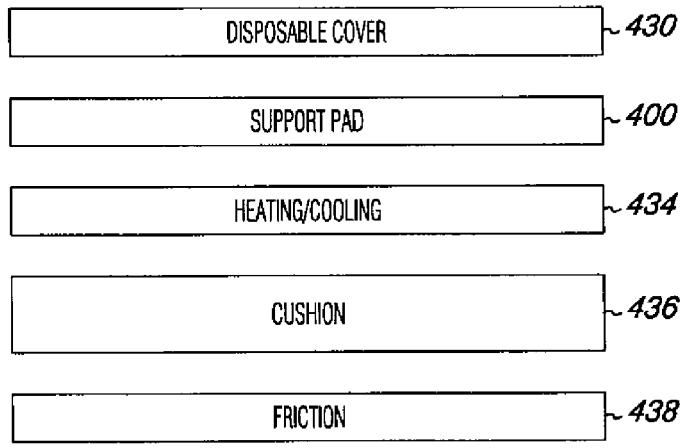
FIG. 4 illustrates a portion of a clinical support system in accordance with one or more embodiments of the present disclosure.

FIG. 4 illustrates a portion of a clinical support system in accordance with one or more embodiments of the present disclosure. In the embodiment illustrated in FIG. 4, the clinical support system includes a disposable cover layer 430, a clinical support pad 400 (e.g., support pad 100 described in connection with FIGS. 1A-1E), a heating/cooling layer 434, a cushion layer 436, and a friction layer 438.

The disposable cover layer 430 can include a fabric layer and/or a microporous layer that can be used as a cover sheet or a sheet enclosing a clinical support pad 400 according to an embodiment of the present disclosure. The disposable layer 430 can provide cleanliness and sterility to prevent infections and can provide comfort for a patient. For instance, a microporous layer can permit perspiration or other moisture associated with the patient to be removed from the location of the patient, and improve the comfort of the patient.

The heating/cooling layer 434 can be a thermoelectric layer and can include heating/cooling components (not shown in FIG. 4) that can be used to heat/cool the support cells of pad 400. The heating/cooling components of layer 434 can be used to inflate/deflate support cells, or can be used to assist with alternating inflation/deflation of the cells (e.g., by heating/cooling the liquid or gas contained therein). The heating/cooling components can be separate electrical circuits with one component being used to heat and cool one cell and heating the other component being used to heat and cool the adjacent cell. Embodiments are not limited to the example illustrated in FIG. 4.

The cushion layer 436 can be used to provide cushioning to and good pressure distribution on clinical support pads of the present disclosure, and thereby can provide improved comfort to the patient. Layer 436 may be formed from a wide variety of fibers or foam materials, including synthetic fibers (e.g., polyamide, polyester and/or polypropylene), natural fibers (e.g., cotton, cellulosic, or wool fibers including sheep skins, etc.). In one or more embodiments, layer 436 may be an air mattress.

In the embodiment illustrated in FIG. 4, the clinical support system includes a friction layer 438. The layer 438 can provide for stability and safety of the patient (e.g., to prevent the support system from sliding off a bed or other structure on which it may be used). The layer 438 can be made of a variety of friction layer materials such as foamed thermoplastic polymers (e.g., polystyrene), woven textile structures, and VELCRO (e.g., a hook and loop fastening structure), to name a few.

Figure 5:
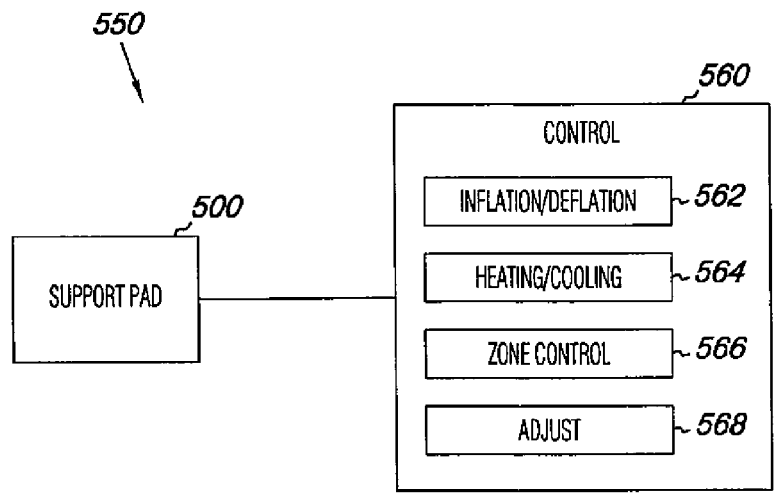
FIG. 5 illustrates a clinical support system in accordance with one or more embodiments of the present disclosure.

FIG. 5 illustrates a clinical support system 550 in accordance with one or more embodiments of the present disclosure. In the embodiment illustrated in FIG. 5, the system 550 includes a clinical support pad 500 coupled to a control component 560. The support pad 500 can be a support pad such as those described in FIG. 1A-1E, 2A, 2B, or 3A-3B, among other support pad in accordance with one or more embodiments of the present disclosure. The control component 560 can be a computing device and can include, and/or can be coupled to, a number of subcomponents.

In the example illustrated in FIG. 5, the control component 560 includes an inflation deflation subcomponent 562, a heating/cooling subcomponent 564, a zone control component 566, and an adjustment component 568. Although not shown in FIG. 5, the control component 560 can include memory storage resources (e.g., RAM, ROM, etc.) and one or more processors capable of executing computer executable instructions storable in the memory to operate one or more embodiments of the present disclosure.

As an example, the inflation deflation component 562 can include one or more pumps and/or fans capable of providing a fluid to and removing a fluid from support cells in a repeating and alternating manner in accordance with one or more embodiments described herein. The cycle of inflation and deflation may be varied, from one minute to in excess of one hour, for example. Different cycles could be used for different areas of the body (e.g., those areas where the body exerts greater pressure could be on a shorter cycle than areas where less pressure is exerted), or different cycles could be used for therapeutic or other reasons.

The inflation and deflation of support cells is generally described herein in the sense that as one cell is inflated, an adjacent cell is deflated. Such inflation and deflation may occur simultaneously or in sequence, the latter involving inflation of a cell followed by deflation of an adjacent cell. In addition, the inflation and deflation may be carried out in the manner of a wave passing across the clinical support system, including according to a peristaltic cycle. One or more embodiments of the present disclosure can provide alternating support for a patient in a manner that the patient has little or no sensation of the alternating support being provided by the clinical support system (e.g., parts of the patient's body are alternately being supported and not supported with the patient having little or no sensation of movement in the bed on which they are lying).

The heating/cooling component 564 can be used to control a heating/cooling layer (e.g., layer 434 described in FIG. 4) that can be used to heat/cool the support cells of pad 500. For example, the heating/cooling component 564 can control one or more electrical circuits used to heat and cool cells in an alternating manner.

The zone control component 566 can be used to operate a number of zones of cells such as described above in connection with FIGS. 2A and 2B, for instance. The number of zones can be separately controlled and the zone control component 566 can adjust the inflation/deflation of the separate zones using the same or different cycle times. For instance, one zone may be configured to cycle every 10 minutes, while a different zone is configured to cycle every 30 minutes, for example. Embodiments are not limited to a particular number of zones or to a particular cycle time corresponding to each zone.

The adjustment component 568 can be used to adjust various parameters of the support system 550. For instance, adjustment component 568 can be used to adjust the amount of pressure being distributed among cells. The adjustment component can also be used to adjust the cycle time associated with the cells of clinical support pad 500. Embodiments are not limited to the examples provided in FIG. 5.

CONCLUSION

Methods, devices, and systems associated with clinical support have been described. Various embodiments can provide benefits such as reducing or eliminating the occurrence of decubitus ulcers (e.g., bedsores or pressure sores). In one embodiment, a clinical support pad includes a plurality of support cells formed in a first film layer of material sufficiently impermeable to a fluid contained in the cells such that each cell is configured to be alternately and repeatedly inflated and deflated with respect to one or more adjacent cells. Each cell is in fluid communication with at least one of a number of channels formed in the first film layer, is configured such that a surface of each cell has a continuous curvature across a length direction and across a width direction of the cell, and are spaced such that a distance between a center of each cell and a center of at least one adjacent cell is not more than a two-point discrimination threshold distance associated with a patient.

Although specific embodiments have been illustrated and described herein, those of ordinary skill in the art will appreciate that an arrangement calculated to achieve the same results can be substituted for the specific embodiments shown. This disclosure is intended to cover adaptations or variations of a number of embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of a number of embodiments of the present disclosure includes other applications in which the above structures and methods are used. Therefore, the scope of a number of embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A clinical support pad, comprising:
   a plurality of support cells formed in a first film layer of material and configured to be alternately and repeatedly inflated and deflated with respect to one or more adjacent cells; and
   a number of channels formed in the first film layer, wherein each cell is in fluid communication with at least one of the number of channels;
   wherein each of the plurality of support cells are configured such that a surface of each cell has a continuous curvature across a length direction and across a width direction of the cell, wherein at least some of the plurality of support cells are ellipsoidal in shape and are described by the equation:

$$\frac{x^2}{a^2} + \frac{y^2}{b^2} + \frac{z^2}{c^2} = 1$$

where x, y, and z are Cartesian coordinates, a and b are equatorial radii, and c is a polar radius; and
   wherein the plurality of support cells are spaced such that a distance between a center of at least one cell and a center of at least one adjacent cell is not more than a two-point discrimination threshold distance associated with a patient such that the patient is unable to distinguish, by touch, the at least one cell from the at least one adjacent cell.

2. The clinical support pad of claim 1, wherein the plurality of support cells are configured to support the patient without bottoming out those of the support cells that are in an inflated condition.

3. The clinical support pad of claim 1, wherein the surface of each cell having a continuous curvature across the width direction of the cell begins and ends on a base surface of the first film layer.

4. The clinical support pad of claim 1, wherein the plurality of support cells are arranged in rows and columns, with the cells of adjacent columns being staggered such that cells of next adjacent columns are aligned as rows of cells.

5. The clinical support pad of claim 4, including:
   a first column of support cells;
   a second column of support cells adjacent to the first column of support cells; and
   a third column of support cells adjacent to the second column of support cells;
   wherein a distance between an edge of a particular support cell of the first column and an edge of a particular support cell of the third column is less than a greatest width of the particular support cell of the first column and of the particular support cell of the third column, in relation to an axis perpendicular to the first column and third column.

6. The clinical support pad of claim 1, wherein each of the plurality of support cells is associated with one or more of a number of zones of cells, with the cells of each zone configured for inflation and deflation substantially concurrently.

7. The clinical support pad of claim 6, wherein the number of zones is at least four, and wherein the cells of each of at least two of the number of zones are in an inflated condition while the cells of at least two of the number of zones are in a deflated condition.

8. The clinical support pad of claim 1, wherein when the support pad is supporting a body of the patient, those cells that are in a deflated condition exert a pressure of less than the human internal capillary threshold on the body of the patient.

9. The clinical support pad of claim 1, including a planar backing layer attached to the first film layer.

10. The clinical support pad of claim 1, wherein selected ones of the plurality of support cells include an orifice providing fluid communication between an interior and an exterior of the cells such that fluid contained therein is gradually released causing the cells to change from an inflated condition to a deflated condition.

11. A clinical support pad, comprising:
   a plurality of support cells configured to be alternately and repeatedly inflated and deflated with respect to one or more adjacent cells;
   wherein the plurality of support cells includes:
      a first column of support cells in fluid communication with each other via a first number of channels;
      a second column of support cells in fluid communication with each other via a second number of channels and adjacent to the first column of support cells; and
      a third column of support cells in fluid communication with each other via a third number of channels and adjacent to the second column of support cells; and
   wherein a distance between an edge of a particular support cell of the first column and an edge of a particular support cell of the third column is less than a greatest width of the particular support cell of the first column and of the particular support cell of the third column.

12. The clinical support pad of claim 11, wherein the plurality of support cells are spaced such that a distance between a center of at least one cell and a center of at least one adjacent cell is not more than a two-point discrimination threshold distance associated with a patient such that the patient is unable to distinguish, by touch, the at least one cell from the at least one adjacent cell.

13. The clinical support pad of claim 11, wherein the edge of the particular support cell of the first column and the edge of the particular support cell of the third column are analogous edges.

14. The clinical support pad of claim 11, wherein selected ones of the plurality of support cells include an orifice providing fluid communication between an interior and an exterior of the cells such that fluid contained therein is gradually released causing the cells to change from an inflated condition to a deflated condition.

15. The clinical support pad of claim 11, wherein each of the plurality of support cells is configured such that a surface of each cell has a continuous curvature across a length direction and across a width direction of the cell.

16. The clinical support pad of claim 15, wherein at least some of the plurality of cells are ellipsoidal in shape and are described by the equation:

$$\frac{x^2}{a^2} + \frac{y^2}{b^2} + \frac{z^2}{c^2} = 1$$

where x, y, and z are Cartesian coordinates, a and b are equatorial radii, and c is a polar radius.

17. The clinical support pad of claim 11, wherein the first column of support cells are in fluid communication with the third column of support cells such that the support cells of the first and third columns are inflated and deflated substantially concurrently.

18. A clinical support pad, comprising:
a plurality of support cells configured to be alternately and repeatedly inflated and deflated with respect to one or more adjacent cells;
wherein each cell is in fluid communication with at least one of a number of channels;
wherein the plurality of support cells are spaced such that a distance between a center of each cell and a center of at least one adjacent cell is not more than a two-point discrimination threshold distance associated with a patient;
wherein each of the plurality of support cells is associated with one or more of a number of zones of cells, with the cells of each zone configured for inflation and deflation substantially concurrently; and
wherein the number of zones is at least four, and wherein the cells of each of at least two of the number of zones are in an inflated condition while the cells of at least two of the number of zones are in a deflated condition.

19. The clinical support pad of claim 18, wherein selected ones of the plurality of support cells include an orifice providing fluid communication between an interior and an exterior of the cells such that fluid contained therein is gradually released causing the cells to change from an inflated condition to a deflated condition.

* * * * *